(12) United States Patent
Das et al.

(10) Patent No.: US 10,682,298 B2
(45) Date of Patent: Jun. 16, 2020

(54) PROCESS FOR PREPARING AN ANTIMICROBIAL PARTICULATE COMPOSITION

(71) Applicant: Conopco, Inc., Englewood Cliffs, NJ (US)

(72) Inventors: Somnath Das, Kolkata (IN); Satyaranjan Gupta, Pune (IN); Rupak Mitra, Bangalore (IN); Girish Muralidharan, Chennai (IN); Amitava Pramanik, Bangalore (IN)

(73) Assignee: CONOPCO, INC., Englewoods Cliffs, NJ (US)

( * ) Notice: Subject to any disclaimer, the term of this patent is extended or adjusted under 35 U.S.C. 154(b) by 0 days.

(21) Appl. No.: 15/326,841

(22) PCT Filed: Jul. 16, 2015

(86) PCT No.: PCT/EP2015/066298
§ 371 (c)(1),
(2) Date: Jan. 17, 2017

(87) PCT Pub. No.: WO2016/020168
PCT Pub. Date: Feb. 11, 2016

(65) Prior Publication Data
US 2017/0209347 A1    Jul. 27, 2017

(30) Foreign Application Priority Data

Aug. 6, 2014 (EP) .................................. 14180010

(51) Int. Cl.
| | |
|---|---|
| *A61K 8/02* | (2006.01) |
| *A61K 8/19* | (2006.01) |
| *A61K 8/27* | (2006.01) |
| *A01N 25/08* | (2006.01) |
| *A01N 59/16* | (2006.01) |
| *A01N 59/20* | (2006.01) |
| *A61Q 17/00* | (2006.01) |
| *A61Q 19/10* | (2006.01) |

(52) U.S. Cl.
CPC ............... *A61K 8/19* (2013.01); *A01N 25/08* (2013.01); *A61K 8/0245* (2013.01); *A61K 8/0279* (2013.01); *A61K 8/0287* (2013.01); *A61K 8/27* (2013.01); *A61Q 17/005* (2013.01); *A61Q 19/10* (2013.01); *A61K 2800/412* (2013.01); *A61K 2800/413* (2013.01); *A61K 2800/651* (2013.01); *A61K 2800/74* (2013.01)

(58) Field of Classification Search
None
See application file for complete search history.

(56) References Cited

U.S. PATENT DOCUMENTS

| | | |
|---|---|---|
| 5,169,682 A | 12/1992 | Asai |
| 2006/0015317 A1 | 1/2006 | Nakagawa |
| 2006/0243675 A1 | 11/2006 | Lin et al. |
| 2008/0156232 A1 | 7/2008 | Crudden et al. |
| 2010/0119461 A1* | 5/2010 | Bicard-Benhamou ........ A01N 59/16 424/49 |
| 2017/0209347 A1 | 7/2017 | Das et al. |

FOREIGN PATENT DOCUMENTS

| | | |
|---|---|---|
| CN | 1777653 | 5/2006 |
| CN | 101195719 | 6/2008 |
| CN | 101999409 | 4/2011 |
| CN | 102781229 | 11/2012 |
| CN | 103200825 | 7/2013 |
| JP | 717803 | 1/1995 |
| JP | 7304616 | 11/1995 |
| JP | 11236304 | 8/1999 |
| JP | 2998061 | 1/2000 |
| KP | 20090018456 | 2/2009 |
| KR | 20060034604 | 4/2006 |
| RU | 2311804 | 12/2007 |
| WO | WO0000166 | 1/2000 |
| WO | WO03076341 | 9/2003 |
| WO | WO2006015317 | 2/2006 |
| WO | WO07139735 | 12/2007 |

(Continued)

OTHER PUBLICATIONS

Długosz et al. "Hybrid calcium carbonate/polymer microparticles containing silver nanoparticles as antibacterial agents", Journal of Nanoparticle Research, 14, 2012, pp. 1-8. (Year: 2012).*
Apalangya et al., Development of antimicrobial water filtration hybrid material from bio source calcium carbonate silver nanoparticles, Appl Surface Sci, 12, pp. 108-114, 2014, US (NPL 1, pp. 1-7).
Dlugosz et al., Hybrid calcium carbonate/polymer microparticles containing silver nanoparticles as antibacterial agents, J Nanopart Res, 2012, pp. 1-8, 14, PL (NPL 1, pp. 8-15).
Moritz et al., Newest achievements in synthesis immobilization and practical applications of antibacterial nanoparticles Chem Eng J, 2013, pp. 596-613, 228, PL (NPL 1, pp. 16-33).
Search Report in EP14180010, dated Sep. 12, 2014 (NPL 1, pp. 34-37).

(Continued)

*Primary Examiner* — Melissa L Fisher
(74) *Attorney, Agent, or Firm* — Krista A. Kostiew

(57) ABSTRACT

The present invention relates to a process for preparing an antimicrobial particulate composition. The invention also relates to personal care or hygiene composition comprising an antimicrobial particulate composition obtainable by the process in accordance with this invention. The invention more particularly relates to a process for preparing an antimicrobial metal nanoparticles immobilized in an inorganic porous material and also incorporating these particles in personal care or hygiene compositions. The antimicrobial particulate composition comprises 0.05% to 3% by weight of antimicrobial metal particles and 97 to 99.95% by weight of immobilizer comprising an inorganic porous material selected from zinc oxide, magnesium hydroxide or calcium carbonate.

7 Claims, No Drawings

(56) References Cited

FOREIGN PATENT DOCUMENTS

| WO | WO2008027950 | 3/2008 | | |
|---|---|---|---|---|
| WO | WO2010046238 | 4/2010 | | |
| WO | WO2011075855 | 6/2011 | | |
| WO | WO-2011075855 A1 * | 6/2011 | ............ | A01N 25/34 |
| WO | WO2012076310 | 7/2012 | | |
| WO | WO2012158702 | 11/2012 | | |
| WO | WO2012161603 | 11/2012 | | |
| WO | WO2014052973 | 4/2014 | | |
| WO | WO2014170186 | 10/2014 | | |
| WO | WO2016020168 | 2/2016 | | |
| WO | WO2017029482 | 2/2017 | | |

OTHER PUBLICATIONS

Search Report in PCTEP2015066298, dated Sep. 18, 2015, WO (NPL 1, pp. 38-42).

Volodkin, CaCO3 templated micro-beads and -capsules for bioapplications, Adv Coll Interface Sci, 2014, pp. 1-19, DE (NPL 1, pp. 43-61).

Written Opinion in EP14180010, dated Sep. 12, 2014 (NPL 1, pp. 62-63).

Written Opinion in PCTEP2015066298, dated Sep. 18, 2015, WO (NPL 1, pp. 64-68).

Search Report and Written Opinion in EP18160896.

IPRP2 in PCTEP2017078601; Mar. 11, 2019; World Intellectual Property Org. (WIPO).

Search Report and Written Opinion in EP16205207; dated Mar. 3, 2017.

Written Opinion 2 in PCTEP2017078601.

Search Report and Written Opinion in EP18161216; dated Jun. 7, 2018; European Patent Office (EPO).

Sahoo et al.; Facile fabrication of silver nanoparticle embedded CaCO3 microspheres via microalgae-templated CO2 biomineralization application in antimicrobial paint development; RSC Advances; 2014; 32562-32569; XP0055478769; vol. 4, No. 61.

Search Report and Written Opinion in PCTEP2017078601; dated Dec. 19, 2017.

Search report and Written Opinion in PCTEP2019055102; dated May 7, 2019.

C. Karunakaran et al; "Antibacterial and photocatalytic activities of sonochemically prepared ZnO and Ag—ZnO", Journal of Alloys and Compounds, (508), 2010, PP587-591; Elsevier B.V.

Co-pending Application, U.S. Appl. No. 16/465,302.

Co-pending Application, U.S. Appl. No. 16/408,664.

* cited by examiner

PROCESS FOR PREPARING AN ANTIMICROBIAL PARTICULATE COMPOSITION

FIELD OF THE INVENTION

The present invention relates to a process for preparing an antimicrobial particulate composition. The invention also relates to personal care or hygiene compositions comprising the antimicrobial particulate composition made by the process. The invention provides antimicrobial metal nanoparticles immobilized in an inorganic porous material and also for incorporating the antimicrobial particulate composition in personal care or hygiene compositions.

BACKGROUND OF THE INVENTION

Any discussion of the prior art throughout the specification should in no way be considered as an admission that such prior art is widely known or forms part of the common general knowledge in the field.

Antimicrobial metal nanoparticles such as silver or copper nanoparticles are broad-spectrum antimicrobial materials used for different purposes including water purification and other hygiene-related products. However, these metal nanoparticles are known to be toxic and cannot be used as such in compositions for human use. They also have an impact on the environment.

The silver or copper nanoparticles have a tendency to agglomerate under certain conditions of pH and temperature which results in lowering of its antimicrobial activity and imparting colouration making the product aesthetically unpleasant and difficult to be incorporated in many products especially when the base is white or light coloured.

WO14052973 A1 (Stelo Technologies), discloses a method of making silver nanoparticles using an ascorbic acid derivative or an alpha-hydroxy carboxylic acid derivative as a reducing agent. The silver nanoparticles may be coated onto micro particles, embedded in hydrogel particles or coated with polysaccharide. The silver nanoparticles may be used in a wound dressing, a bandage, a fungal treatment product, a deodorant, a floss product, a toothpick, a dietary supplement, dental X-ray, a mouthwash, a toothpaste, acne or wound treatment product, skin scrub, and skin defoliate agent. In this process which comprises mixing silver salt with the reducing agent and then coprecipitating the nanoparticles formed on microparticles, the colour of the composite particles will be dark and will be unsuitable for personal care products especially when they have a white base.

KR20090018456 (Korea University Industrial and Academic Collaboration Foundation), discloses the preparation of silver zinc oxide nanocomposite by simultaneous mixing of silver and zinc sources with reducing agents in ethanolic medium. Simultaneous mixing of zinc source and silver salt leads to undesired dark coloration and lowers the antimicrobial efficacy.

RU2311804 C1 (Megrabjan), discloses bactericidal composition containing highly dispersed metallic silver stabilized with a protective material. The material was prepared by mixing silver salt, calcium salt and a base, which would lead to undesired dark coloration and lower antimicrobial efficacy.

JP11236304 (Dowa Electronics Materials Corp.), discloses a method of preparing silver particles embedded in calcium carbonate by a process of mixing silver salt and calcium carbonate and then calcining the material. The material obtained would have the problem of dark coloration and lower antimicrobial efficacy.

US2008/0156232 A1 (Crudden et.al, 2008) discloses a process for preparing antimicrobial additive particles in which the antimicrobial agent is dry blended with a cake-forming material and thereafter this dry blend is added to water. After this step, the aqueous slurry is allowed to harden.

WO2012/161603 A1 (Uniwersytet Jagiellonski) discloses yet another method. Hybrid material containing calcium carbonate microparticles with a polyelectrolyte additive and silver nanoparticles embedded in its structure are made by ultrasound-assisted co-precipitation. Trisodium citrate is added to aqueous solution of Silver nitrate followed by sonication at elevated temperature. To this a solution of Sodium carbonate containing a polyelectrolyte and calcium nitrate is added which subsequently leads to nano-Silver particles embedded in a matrix.

WO2011/075855 A1 (Perlen Converting AG) discloses a method in which the composite material is made by flame-spray pyrolysis.

WO2003/076341 A1 (Apyron Technologies INC) also discloses particulate matter containing a carrier and an antimicrobial agent.

WO2006/015317 A1 (Acrymed INC), discloses a process for making silver compounds by mixing stoichiometric amounts of solutions of a silver salt such as silver nitrate or acetate with a corresponding alkali or alkaline earth metal salt of an organic anionic compound. When preparing silver compounds dispersed on carrier supports, the mixing step is carried out in the presence of insoluble carrier materials.

WO2012/158702 A1 (BASF) discloses a process of preparing antimicrobial metal composite by vaporizing an antimicrobial metal or antimicrobial metal salt such as silver, copper or salts thereof using an plasma system and cooling the formed vapour in the presence a fluidized gas filler powder. Alternatively, the filler or a filler precursor is entrained with the antimicrobial metal or antimicrobial metal precursor and vaporized and then upon cooling the antimicrobial metal vapour and filler vapor condense to form the composite.

U.S.2006/0243675 A1 (Shiue-Lian Lin) discloses a process in which the components are added to pure water and mixed and then the mixture is maintained 3 to 5 hours to produce a homogeneous mixture readily for use in the next step. In this process, no reducing agent is used.

WO2008/027950 A1 (Allen Thomas) discloses a process in which metal particles like silver, copper, or gold together with a surfactant such as benzalkonium chloride, are taken in a liquid medium also having a source of iodine and a substrate carrier having the same type of metal as the particles deposited onto. This leads to embedded microparticles CN101999409 (Henan Huier) discloses a process in which 15 to 70 mass % of deionized water or tap water is placed for 16 to 36 hours at room temperature into a reactor. Solution of a nano carrier with zinc is added to the reactor which is then dispersed and emulsified under high-speed mixing and shearing for 6 to 20 minutes, while maintaining the temperature of liquid at 5 to 25 degree Celcius. Then a solution of a silver salt is added into the reactor and continuously dispersed and emulsified for 40 to 90 minutes. This is followed by spraying a solution of a reducing agent into the reactor at rate of 1.5 to 9.5 kg/minute continuously dispersed and emulsified for 30 to 60 minutes to obtain the antimicrobial disinfectant.

CN101195719 B (Cao) discloses composite material containing a carrier and antibacterial metal.

It has now been possible to solve the problems of the prior art and to form a light-coloured, broad spectrum antimicrobial particulate composition with good antimicrobial properties comprising antimicrobial metal particles and porous inorganic material selected from water insoluble inorganic materials and also provide a process for preparing the same.

It is an object of the present invention to provide light coloured antimicrobial particulate composition that has good antimicrobial properties.

Another object is to provide a process for preparing antimicrobial particulate composition that has good antimicrobial properties.

It is yet another object of the present invention to provide an antimicrobial particulate composition that has good antimicrobial properties and aesthetically suitable for incorporation in personal care or hygiene compositions. It is especially beneficial for use where the base of the personal care or hygiene composition is white or light coloured.

In addition to killing bacteria, these materials are also capable of acting in killing virus.

SUMMARY OF THE INVENTION

According to the present invention there is provided a process for preparing an antimicrobial particulate composition the process comprising the steps of:
  i. mixing an aqueous dispersion of an immobiliser, wherein the immobiliser is present in an amount of 1-5 wt % (by weight of the dispersion) and wherein the immobilizer is selected from inorganic porous material selected from zinc oxide, magnesium hydroxide or calcium carbonate and wherein the immobiliser has a particle size in the range of 1-10 microns and
    an aqueous solution of a reducing agent, wherein the reducing agent is present in the aqueous solution in an amount of from 10 to 30 wt % by weight of the immobilizer in the aqueous dispersion;
  ii. raising the temperature of the mixture resulting from step (i) to a temperature in the range 70° C. to 90° C.;
  iii. adding a water soluble metal salt to the mixture resulting from step (ii) in an amount equivalent to 0.05 to 3 wt % of the metal by weight the immobilizer under mixing.

According to yet another aspect of the present invention there is provided a personal care or hygiene composition comprising:
  i. 5% to 85% by weight of a surfactant and
  ii. 0.1 to 5% by weight an antimicrobial particulate composition obtainable by the process of the invention.

DETAILED DESCRIPTION OF THE INVENTION

These and other aspects, features and advantages will become apparent to those of ordinary skill in the art from a reading of the following detailed description and the appended claims. For the avoidance of doubt, any feature of one aspect of the present invention may be utilized in any other aspect of the invention. The word "comprising" is intended to mean "including" but not necessarily "consisting of" or "composed of." In other words, the listed steps or options need not be exhaustive. It is noted that the examples given in the description below are intended to clarify the invention and are not intended to limit the invention to those examples per se. Similarly, all percentages are weight/weight percentages unless otherwise indicated. Except in the operating and comparative examples, or where otherwise explicitly indicated, all numbers in this description and claims indicating amounts of material or conditions of reaction, physical properties of materials and/or use are to be understood as modified by the word "about". Numerical ranges expressed in the format "from x to y" are understood to include x and y. When for a specific feature multiple preferred ranges are described in the format "from x to y", it is understood that all ranges combining the different endpoints are also contemplated.

The antimicrobial particulate composition made in accordance with the invention comprises 0.05% to 3% by weight of antimicrobial metal particles and 97 to 99.95% by weight of immobilizer comprising inorganic porous material selected from zinc oxide, magnesium hydroxide or calcium carbonate.

The weight % of the antimicrobial metal particles and the immobilizer in the antimicrobial particulate composition is by weight of the composition.

Antimicrobial Metal Particles:

It is preferred that the antimicrobial metal particles are preferably selected from silver or copper particles, more preferably from silver or copper nanoparticles and most preferably are silver nanoparticles.

Immobilizer:

The immobilizer is selected from an inorganic porous material selected from porous zinc oxide, magnesium hydroxide or calcium carbonate and it is preferred that the inorganic porous materials have a nano/micro-structured assembly and more preferably are aggregates of nano plate like structures having preferably 20-100 nm width and more preferably 40-60 nm width. It is preferred that the immobilizer has a particle size in the range of 1-10 microns and more preferably 2 to 5 microns. The immobilizer is preferably selected from porous zinc oxide or calcium carbonate.

The inorganic porous materials that have nano plate like structures are preferably obtained from a commercial source or can be prepared by a standard precipitation process that promote formation of porous structures, by using crystal habit modifiers or by precisely controlling the precipitation conditions. Porous calcium carbonate used is preferably vaterite polymorph and porous zinc oxide is preferably prepared by standard precipitation process that promotes the formation of porous structures, by using crystal habit modifiers. Porous magnesium hydroxide is preferably obtained from calcination of light magnesium carbonate and such materials are also commercially available.

The antimicrobial particulate composition comprises 0.05% to 3% by weight of antimicrobial metal particles preferably immobilized in 97 to 99.95% by weight of an immobilizer comprising inorganic porous material selected from zinc oxide, magnesium hydroxide or calcium carbonate. Preferably the antimicrobial particulate composition comprises 0.5% to 1.5% by weight of antimicrobial metal particles and 98.5% to 99.5% by weight of an immobilizer. In general when reference is made to immobilized antimicrobial particles or immobilized antimicrobial metal particles or immobilized metal nanoparticles or immobilized materials with reference to specific metals such as silver or copper, it refers to antimicrobial particulate composition of the invention.

According to the present invention there is provided process for preparing an antimicrobial particulate composition and the process comprising the steps of:
  i. mixing an aqueous dispersion of an immobiliser, wherein the immobiliser is present in an amount of 1-5 wt % (by weight of the dispersion) and wherein the immobilizer is selected from inorganic porous material selected from zinc oxide, magnesium hydroxide or calcium carbonate and wherein the immobiliser has a particle size in the range of 1-10 microns and an aqueous solution of a reducing agent, wherein the reducing agent is present in the aqueous solution in an amount of from 10 to 30 wt % by weight of the immobilizer in the aqueous dispersion;

ii. raising the temperature of the mixture resulting from step (i) to a temperature in the range 70° C. to 90° C.;

iii. adding a water soluble metal salt to the mixture resulting from step (ii) in an amount equivalent to 0.05 to 3 wt % of the metal by weight the immobilizer under mixing.

The antimicrobial particulate composition prepared by the process according to the invention is preferably recovered by separating the solid from the liquid medium by preferably filtration and the antimicrobial particulate composition was preferably dried at a temperature in the range of 10-80° C.

A calcination step is preferably not required for the process according to the invention and preferably the process does not comprise a calcination step.

Immobilizer:

The immobilizer used in the process is in the range of 1-5% and more preferably 2 to 4% and is selected from inorganic porous material selected from porous zinc oxide, magnesium hydroxide or calcium carbonate. The particle size is in the range 1-10 microns and more preferably 2 to 5 microns. The immobilizer is used as an aqueous dispersion. It is preferred that the immobilizer is selected from porous zinc oxide or calcium carbonate.

Reducing Agent:

The reducing agent is preferably selected from water soluble salt of a carboxylic acid with a 1-4 carboxylate group and more preferably it is selected from sodium acetate, sodium oxalate, trisodium citrate or disodium ethylene diamine tetra acetate. It is preferred to include trisodium citrate as the reducing agent. The reducing agent is used in the range 10-30% by weight with respect to immobilizer and more preferably 15 to 20% by weight with respect to immobilizer. The reducing agent is preferably provided as an aqueous solution.

It is essential that the aqueous dispersion of the immobilizer and the aqueous solution of the reducing agent are mixed before adding the metal salt solution. The temperature of the mixture is raised to a temperature in the range 70° C. to 90° C. and more preferably 80° to 85° C.

The pH of the reaction medium during the process is maintained preferably at pH greater than 5 and more preferably is in the range 6-8.

Water Soluble Metal Salt:

It is preferable that the water soluble metal salt is selected from water soluble salt of silver or of copper. It is preferable to add the water soluble metal salt as an aqueous solution.

It is preferable that the water soluble silver salt is selected from silver nitrate or silver acetate. 0.05% to 3% of silver by weight of an immobilizer that is delivered preferably through an aqueous solution is preferably silver nitrate or silver acetate. To deliver the required % weight of silver, the range of silver nitrate preferably is 0.08% to 4.72% by weight or 0.078% to 4.63% by weight of silver acetate. It is preferred to use silver nitrate as the water soluble salt of silver.

It is preferable that the water soluble copper salt is selected from copper (II) sulphate, copper (II) nitrate, copper (II) chloride, and copper (II) acetate. 0.05% to 3% of copper by weight of an immobilizer is delivered preferably through an aqueous solution of copper salt in the range between 0.1% to 9%, more preferably in the range of 0.13% to 7.5% for copper (II) sulphate, 0.15% to 8.9% for copper (II) nitrate, 0.1% to 6.4% for copper (II) chloride and 0.14% to 8.6% for copper (II) acetate. It is preferred to use copper (II) nitrate as the water soluble salt of copper.

According to yet another aspect of the present invention there is provided a personal care or hygiene composition comprising:

i. 5% to 85% by weight of a surfactant and ii. 0.1 to 5% by weight of an antimicrobial particulate composition obtainable by a process in accordance with the present invention.

The level of the surfactant in the personal care composition is 5% to 85% by weight of the personal care or hygiene composition and preferably 15-40% by weight.

The surfactant is selected from class of anionic, non-ionic, cationic or zwitterionic surfactants and preferably selected from anionic surfactants. The anionic surfactant is preferably selected from soap or non-soap surfactant.

It is preferred that the antimicrobial particulate composition is 0.1 to 5% by weight of the personal care composition or hygiene composition and more preferably 0.25 to 4% by weight of the personal care or hygiene composition.

The personal care or hygiene composition of the present invention can be in the form of liquid or solid compositions. Non-limiting examples of such topical compositions include leave-on skin lotions and creams, antiperspirants, deodorants, lipsticks, foundations, mascara, sunless tanners or sunscreen lotions, and wash-off products like shampoos, conditioners, shower gels, or toilet bars.

It is preferable that the composition comprises conventional ingredients used in a personal care or hygiene composition and more preferably ingredients such as fluorescers, perfumes, texture controlling agents, emollients, and other antimicrobial agents.

The invention will now be illustrated by means of the following non-limiting examples.

EXAMPLES

Example 1

Preparation of antimicrobial particulate composition comprising silver nanoparticles
Preparation of the Immobilizer:

Micron sized particles of the immobilizer were prepared by the process described below:

i. Porous zinc oxide:

Porous zinc oxide was prepared by a process as described in CrystEngComm 15, 32 (2013), pp. 6349-6358. For preparing 100 g of porous zinc oxide, 60 g of zinc nitrate and 140 g of hexamine was mixed with trisodium citrate, where the ratio of the concentration of zinc to the concentration of trisodium citrate was maintained at 10, and the mixture was heated in a stoppered hydrothermal container at 90° C. for 12 hours. The precipitated porous zinc oxide was filtered, washed with deionised water and dried in air.

ii. Porous Calcium carbonate:

100 g of porous calcium carbonate was prepared by mixing 147 g of calcium chloride with 106 g sodium carbonate under constant stirring at 10° C. for 5 hours. The slurry was aged for 5 hours, filtered, washed with deionised water and dried in air.

iii. Porous magnesium hydroxide:

Magnesium oxide of light, pure grade was purchased from Merck. Magnesium oxide was dispersed in water to get porous magnesium hydroxide which was used as the immobilizer.

Preparation of the Antimicrobial Particulate Composition Comprising Silver Nanoparticles:

400 mg of immobilizer which was porous zinc oxide or calcium carbonate or magnesium hydroxide was dispersed in 10 mL water and mixed with 4 mL of 1% trisodium citrate solution. The mixture was heated to 80° C. followed by the addition of freshly-prepared 0.25 mL of 2% silver nitrate. The mixture was stirred for 20 minutes at 300 rpm. The sample was filtered and dried at room temperature. The size of the silver nanoparticles formed in the above process ranged between 5-50 nm and the silver nanoparticles get immobilized in the respective immobilizer.

Evidence for Silver Incorporation in the Immobilizer:

Energy-dispersive X-ray spectroscopic analysis of antimicrobial particulate composition comprising silver nanoparticles and porous zinc oxide prepared by the process described in Example 1 was carried out using a FESEM instrument (ZEISS) operated at 10 kV electron voltage to determine the presence of silver in the antimicrobial particulate composition. The analyzed weight % of different ingredients is shown in table 1 below:

TABLE 1

| Element | Weight (%) |
|---|---|
| Oxygen | 23.60 |
| Zinc | 73.09 |
| Silver | 3.31 |
| Total | 100.00 |

Results in table 1 show that the antimicrobial particulate composition contains zinc, oxygen and silver as constituents.

Reflectance of the Antimicrobial Particulate Composition Comprising Silver Nanoparticles:

Reflectance of antimicrobial particulate composition comprising silver nanoparticles where the immobilizer used was zinc oxide, calcium carbonate or magnesium hydroxide and prepared as described in Example 1, was measured.

In the comparative example (Example 5) where commercial zinc oxide which was not porous was used to immobilize the silver nanoparticles, otherwise using the same process. In another comparative example (Example 6), a process according to prior art was used where the immobilization of the silver particles was done by calcination. In this process the porous zinc oxide was used without using the reducing agent and at the end of the process the material was calcined by heating it to a temperature of 500° C.

Reflectance of the materials described above were measured using Gretag Macbeth reflectometer at 460 nm in the SCI, SAV mode, UV excluded condition. A film of the dispersion of immobilized silver nanoparticles was prepared on a glass slide having an area of 4 cm×4 cm. The film was dried and reflectance was measured. The b* values measured indicate the dullness index. Negative b* values indicate the closeness to whitish colouration and b* values less than −0.5 indicate near whitish coloration. The data is presented in table 2.

TABLE 2

| Examples | Material | b* |
|---|---|---|
| Example 2 | Silver nanoparticles immobilized in porous zinc oxide | −1.1 |
| Example 3 | Silver nanoparticles immobilized in porous calcium carbonate | −8.0 |
| Example 4 | Silver nanoparticles immobilized in porous magnesium hydroxide | −1.9 |
| Example 5 | Silver nanoparticles immobilized in non-porous rod shape zinc oxide | 5.0 |
| Example 6 | Silver nanoparticles immobilized in porous zinc oxide by a process of calcination | 3.6 |

The data presented in table 2 show that antimicrobial particulate composition prepared according to the invention have a negative b* value indicating a better desired color profile which can be used in the formulations without affecting the product aesthetics. In the comparative examples where the immobilizer used was non-porous zinc oxide and had a rod shaped structure or where the process of immobilizing silver particles was done by a calcination process, the immobilized materials had a relatively high b* values indicating a dark colouration.

Variation in Process Parameters of Efficacy:

Preparation of the antimicrobial particulate composition comprising silver nanoparticles was done by changing the concentration of the immobilizer, silver nitrate or trisodium citrate. For all these experiments, zinc oxide was used as the immobilizer.

The reflectance of the antimicrobial particulate composition comprising silver nanoparticles obtained was measured as described above to evaluate the b* value to indicate the coloration of the material and the results are presented in table 3. In table 3, under the process condition column, the weight % of porous zinc oxide is with respect to the volume of water while the percentages of silver and trisodium citrate are with respect to the porous zinc oxide. All percentage values mentioned in table 3 correspond to amount of ingredients used during preparation of antimicrobial particulate composition comprising silver nanoparticles. The product composition column indicates the weight % of silver and porous zinc oxide after immobilization of silver nanoparticles.

TABLE 3

| | | Process condition | | | | | | Product composition | | |
|---|---|---|---|---|---|---|---|---|---|---|
| | | Porous zinc oxide | | Silver | | Trisodium citrate | | Ag | ZnO | |
| Example No. | Process variation | mg | wt % | mg | wt % | mg | wt % | wt % | wt % | b* |
| 7 | Variation of porous zinc oxide concentration | 250 | 2.5 | 6.35 | 2.5 | 40 | 16 | 2.5 | 97.5 | −5.92 |
| 8 | | 400 | 4 | 6.35 | 1.6 | 40 | 10 | 1.6 | 98.4 | −5.36 |
| 9 | | 1000 | 10 | 6.35 | 0.6 | 40 | 4 | 0.6 | 99.4 | −0.45 |

TABLE 3-continued

|  |  | Process condition | | | | | | Product composition | | |
|---|---|---|---|---|---|---|---|---|---|---|
|  |  | Porous zinc oxide | | Silver | | Trisodium citrate | | Ag | ZnO |  |
| Example No. | Process variation | mg | wt % | mg | wt % | mg | wt % | wt % | wt % | b* |
| 10 | Variation | 400 | 4 | 1.27 | 0.3 | 40 | 10 | 0.3 | 99.7 | −12.3 |
| 8 | of silver | 400 | 4 | 6.35 | 1.6 | 40 | 10 | 1.6 | 98.4 | −5.36 |
| 11 | concentration | 400 | 4 | 25.41 | 6.0 | 40 | 10 | 6.0 | 94.0 | +13.9 |
| 12 |  | 400 | 4 | 63.53 | 13.7 | 40 | 10 | 13.7 | 86.3 | +1.1 |
| 13 | Variation | 400 | 4 | 6.35 | 1.6 | 20 | 5 | 1.6 | 98.4 | +3.84 |
| 8 | of trisodium | 400 | 4 | 6.35 | 1.6 | 40 | 10 | 1.6 | 98.4 | −5.36 |
| 14 | citrate concentration | 400 | 4 | 6.35 | 1.6 | 120 | 30 | 1.6 | 98.4 | −10.9 |

The data presented in table 3 shows that variation in process parameters during the preparation antimicrobial particulate composition using silver nanoparticles and porous zinc oxide. The b* value becomes more positive with increase in porous zinc oxide weight % (Example 9) while increase in silver weight % leads to positive b* value (Example 11 and 12). Alternatively, lowering of trisodium citrate weight % below 10 leads to positive b* value (Example 13). Overall for most optimal result as shown in table 3 for obtaining b* value less than 0.5, the aqueous weight percentage of porous zinc oxide is in the range of 1-5, and the weight percentage of citrate and silver with respect to porous zinc oxide is in the range of 10-30 and 0.05-3 respectively.

Sequence of the Process Steps:

The sequence of addition of materials according to the present invention where the aqueous dispersion of the immobilizer is mixed with the aqueous solution of a reducing agent such as trisodium citrate followed by the addition of the antimicrobial silver nitrate was compared with a process where the antimicrobial silver nitrate was added before the addition of the reducing agent or where the process of preparation of porous zinc oxide as described earlier in Example 1 was carried out in the presence of silver nitrate otherwise using the same process. In the processes the levels of the various materials were as in Example 8.

The reflectance of the immobilized material obtained was measured as described above to evaluate the b* value to indicate the coloration of the material and the results are presented in table 4.

TABLE 4

| Example | Process | b* |
|---|---|---|
| Example 8 | Addition of trisodium citrate to porous zinc oxide followed by silver nitrate | −5.4 |
| Example 15 | Addition of silver nitrate to porous zinc oxide followed by trisodium citrate | +13.5 |
| Example 16 | Hydrothermal treatment of zinc nitrate and hexamine in the presence of trisodium citrate and silver nitrate | +12.6 |

The data presented in table 4 show that the addition of trisodium citrate to zinc oxide followed by silver nitrate yields antimicrobial particulate composition according to the invention with negative b* value (Example 8) while the addition of silver nitrate to zinc oxide followed by trisodium citrate yields positive b* value (Example 15). Also, formation of porous zinc oxide in the presence of silver nitrate yields again positive b* value (Example 16).

Antimicrobial Efficacy:

The antimicrobial efficacy was tested using gram positive bacteria *Staphylococcus aureus* and gram negative bacteria *Escherichia coli* bacteria by using Time kill assay according to BS EN1040 protocol.

10 g soap was dissolved in 90 mL water at 50° C. It was allowed to equilibrate to a temperature of 45° C. in a water bath. Antimicrobial particulate composition comprising silver nanoparticles was added to the soap solution to get 1 ppm effective silver load and the same was calculated by ICP-OES analysis. 1 mL bacterial suspension of *Staphylococcus aureus* ($10^8$ cells/mL) and *E. coli* ($10^8$ cells/mL), respectively, was added to the tubes containing 1 mL sterile water and was allowed to equilibrate at 45° C. for 2 minutes. 8 mL of 10% soap solution containing antimicrobial particulate composition comprising silver nanoparticles was added to these bacterial suspensions respectively and was allowed to act for 30 seconds and 60 seconds respectively. On these respective time points, 1 mL suspension was taken and added to 9 mL of neutralizer (Dey-Engley Neutralizing Broth) to inactivate the action of the antimicrobial. The neutralized samples were then plated after serial dilution in Trypticase Soy Agar (nutrient medium) to enumerate the residual bacteria. The efficacy of the antimicrobial particulate composition comprising silver nanoparticles was also evaluated with Methicillin-resistant *Staphylococcus aureus* (MRSA) at 60 and 300 seconds respectively. The results are presented in Table 5.

TABLE 5

|  |  | Bacterial reduction (log CFU/mL) | | | | | |
|---|---|---|---|---|---|---|---|
|  |  | *E. coli* | | *S. aureus* | | MRSA | |
| Example | Material | 30 s | 60 s | 30 s | 60 s | 60 s | 300 s |
| Example 17 | Soap | 3.4 | 3.5 | 0.0 | 0.1 | 0.3 | 1.2 |
| Example 18 | Soap + Porous zinc oxide | 3.9 | 6.3 | 0.0 | 0.2 | — | — |
| Example 19 | Soap + Silver nitrate | 6.3 | 7.7 | 4.2 | 5.2 | — | — |
| Example 20 | Soap + silver nanoparticle | 3.7 | 7.0 | 4.8 | 6.0 | — | — |
| Example 21 | Soap + silver nanoparticles immobilized in zinc oxide | 7.6 | 6.7 | 5.1 | 6.7 | 2.0 | 4.6 |

TABLE 5-continued

| Example | Material | Bacterial reduction (log CFU/mL) | | | | | |
|---|---|---|---|---|---|---|---|
| | | E. coli | | S. aureus | | MRSA | |
| | | 30 s | 60 s | 30 s | 60 s | 60 s | 300 s |
| Example 22 | Soap + silver nanoparticles immobilized in calcium carbonate | 8.1 | 8.1 | 4.8 | 6.8 | 1.8 | 4.9 |
| Example 23 | Soap + silver nanoparticles immobilized in magnesium hydroxide | 5.2 | 7.8 | 3.9 | 5.4 | — | — |

The data in table 5 shows that immobilized silver nanoparticles (Example 21-23) have superior bacterial reduction against both *E.coli* and *S.aureus* when compared to any of its individual constituents. Even though the silver nitrate and silver nanoparticle with soap shows comparative antimicrobial action, its use is limited as silver nitrate being unstable can't be formulated in products while the use of only nanoparticles has issues related to agglomeration, instability upon storage and environmental hazards. The data also shows that the immobilized silver nanoparticles have antimicrobial action against MRSA with 5 log reduction at 300 s.

No efficacy validation tests were performed on the immobilizers per se, used in Example 22 and Example 23, as there are no literature evidence on antimicrobial activity of either calcium carbonate (immobilizer in Example 22) or magnesium hydroxide (immobilizer in Example 23).

The invention claimed is:

1. A process for preparing an antimicrobial particulate composition the process comprising the steps of:
   i. mixing an aqueous dispersion of an immobilizer, wherein the immobilizer is present in an amount of 1-5 wt % (by weight of the dispersion) and wherein the immobilizer is selected from inorganic porous material selected from zinc oxide, magnesium hydroxide or calcium carbonate and wherein the immobilizer has a particle size in the range of 1-10 microns and
      an aqueous solution of a reducing agent, wherein the reducing agent is present in the aqueous solution in an amount of from 10 to 30 wt % (by weight of the immobilizer in the aqueous dispersion);
   ii. raising the temperature of the mixture resulting from step (i) to a temperature in the range 70° C. to 90° C.;
   iii. adding a water soluble metal salt to the mixture resulting from step (ii) in an amount equivalent to 0.05 to 3% of the metal by weight of the immobilizer under mixing.

2. The process according to claim 1, wherein the water soluble metal salt is selected from water soluble salts of silver or of copper.

3. The process according to claim 1, wherein the water soluble metal salt is a water soluble salt of silver.

4. The process according to claim 3, wherein the water soluble salt of silver is selected from silver nitrate or silver acetate.

5. The process according to claim 2, wherein the water soluble salt of copper is selected from copper (II) sulphate, copper (II) nitrate, copper (II) chloride, or copper (II) acetate.

6. The process according to claim 1, wherein the reducing agent is selected from a water soluble salt of a carboxylic acid, wherein the reducing agent has 1 to 4 carboxylate groups.

7. The process according to claim 1, wherein the reducing agent is selected from sodium acetate, sodium oxalate, trisodium citrate or disodium ethylene diamine tetra acetate.

* * * * *